United States Patent [19]

Brink et al.

[11] Patent Number: 5,563,034
[45] Date of Patent: Oct. 8, 1996

[54] NEGATIVE CONTROL PROBES THAT ARE IDENTICAL IN SEQUENCE BUT OPPOSITE IN POLARITY TO THE TARGET, OR ARE COMPLEMENTARY IN SEQUENCE AND OF THE SAME POLARITY AS THE TARGET, FOR USE IN NUCLEIC ACID HYBRIDIZATION ASSAYS

[76] Inventors: Donald E. Brink, P. O. Box 671327, Chugiak, Ak. 99567-1327; K. Jane Aldrich, 6447 18th St. Apt. 9, Berwyn, Ill. 60402

[21] Appl. No.: 225,323

[22] Filed: Apr. 8, 1994

Related U.S. Application Data

[63] Continuation-in-part of Ser. No. 941,874, Sep. 8, 1992, abandoned, which is a continuation-in-part of Ser. No. 705,577, May 24, 1991, abandoned, which is a division of Ser. No. 339,277, Apr. 17, 1989, Pat. No. 5,049,489.

[51] Int. Cl.$^6$ ............................. C12Q 1/68; C07H 21/04
[52] U.S. Cl. ............................. 435/6; 536/24.3; 935/77; 935/78
[58] Field of Search ..................... 435/6; 536/24.3, 536/24.31, 24.32; 935/77, 78

[56] References Cited

U.S. PATENT DOCUMENTS 5,434,047  7/1995  Arnold, Jr. ........................ 435/6

OTHER PUBLICATIONS

Giovannoni et al. (Feb. 1988) J. Bacteriol. 170(2): 720–726.

*Primary Examiner*—Lisa B. Arthur
*Attorney, Agent, or Firm*—Nixon & Vanderhye

[57] ABSTRACT

Two basic design criteria for producing oligonucleotide "negative control probes" for use in nucleic acid hybridization assays are described. Each type of negative control probe also functions as a synthetic polynucleotide "target" that is useful for testing the other type of negative control probe. These design criteria also provide structures that are not naturally occurring, but are analogous to naturally occurring nucleic acids in primary, secondary and tertiary structure. These design criteria are useful in hybridization assays and potentially in other applications as well.

1 Claim, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 31 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CCCTCTCAGG CCGGCTACCC ATCGTCGCCT T 31

NEGATIVE CONTROL PROBES THAT ARE IDENTICAL IN SEQUENCE BUT OPPOSITE IN POLARITY TO THE TARGET, OR ARE COMPLEMENTARY IN SEQUENCE AND OF THE SAME POLARITY AS THE TARGET, FOR USE IN NUCLEIC ACID HYBRIDIZATION ASSAYS

CROSS-REFERENCE TO RELATED APPLICATIONS

This application is a continuation-in-part of our earlier application Ser. No. 07/941,874, filed Sep. 8, 1992 abandoned which is a continuation-in-part of Ser. No. 07/705,577 filed May 24, 1991 abandoned which, in turn, is a division of application Ser. No. 07/339,277 filed Apr. 17, 1989, now U.S. Pat. No. 5,049,489.

BACKGROUND OF THE INVENTION

This invention describes two basic design criteria for producing oligonucleotide "negative control probes" for use in nucleic acid hybridization assays. Each type of negative control probe also functions as a synthetic "target" that is useful for testing the other type of negative control probe. These design criteria also provide structures that are not naturally occurring, but are analogous to naturally occurring nucleic acids in primary, secondary and tertiary structure. These design criteria are useful in hybridization assays and potentially in other applications as well.

Examples of embodiments of this invention relate to procedures for detecting and identifying sulfate-reducing bacteria, or SRBs, and more particularly, to the use of oligonucleotide probes complementary to portions of the 16S rRNA molecule of these bacteria to detect and identify sporing and non-sporing sulfate-reducing bacteria and distinguishing them from other bacteria that may also be present in an environmental sample.

BRIEF DESCRIPTION OF THE DRAWINGS

Concepts of oligonucleotide probe design and structures analogous to naturally occurring nucleic acids in primary, secondary and tertiary structure are illustrated with reference to a specific structure, in this case the secondary structure of a small portion of 16S rRNA of a sulfate-reducing bacterium. Various constructs are depicted in the attached drawings in which.

DESCRIPTION OF THE INVENTION

Probes can bind non-specifically to impurities in environmental samples, yielding a "false positive" result. The magnitude of the false positive signal is ascertained using "control" probes that will not bind to rRNA. Signal obtained using control probes is then subtracted from the signal obtained using the experimental probes to determine the amount of signal from true hybridization of experimental probes with rRNA. The complement of all the probes was tested against crude cell lysates in filter and solution hybridizations as well as against isolated RNA. These probes, which will not react with 16S rRNA, but will detect the gene in the genomic DNA, serve as "control" probes. Probes directed to the 16S rRNA molecule theoretically give a signal that is roughly 250–1500 times stronger than that of the complement because the 16S rRNA molecule is present at about 10,000 to 20,000 copies per cell whereas its copy in the chromosome (2 genomes per actively growing cell; Ingraham et al., supra) is present at about 14 copies per cell. If the signal from the 16S rRNA assay is real, it should theoretically be ca. 700–1400 (10,000/14–20,000/14) times greater than that of the signal from the control probe. Actual results showed a signal differential of roughly 500 fold. Control probes can thus help distinguish true positives from false positives.

Another type of negative control probe that was successfully employed is the use of an oligonucleotide identical in sequence to the rRNA "target" (except for the substitution of T for U), but of opposite polarity. We are calling this the "type I" negative control. Alternatively, the negative control probe can be constructed that it would be complementary to the rRNA target, except that it has the same polarity. We are calling this the "type II" negative control. For example, negative controls for the Universal C probe were designed as follows:

| | |
|---|---|
| 3' TGCCCGCCACACAYG 5' | genomic DNA "anti-sense" strand |
| 5' ACGGGCGGTGTGTRC 3' | genomic DNA "sense" strand |
| 3' UGCCCGCCACACAYG 5' | target on 16S rRNA molecule |
| 5' ACGGGCGGTGTGTRC 3' | probe directed to 16S rRNA molecule (will also bind DNA "anti-sense" strand) |
| 5' GYACACACCGCCCGT 3' | negative control probe (complement of the probe, does not bind to rRNA, will bind to DNA "sense" strand) |
| 5' TGCCCGCCACACAYG 3' | Type I negative control probe (does not bind rRNA or genomic DNA) |
| 3' ACGGGCGGTGTGTRC 5' | Type II negative control probe (does not bind rRNA or genomic DNA) | where R=A or G and Y=T or C

Negative control probes will bind to neither the 16S rRNA molecule nor its gene in the genomic DNA. Negative control probes for all probes designed to detect 16S rRNA were tested in solution hybridizations described below. These probes did not bind to 16S rRNA in crude cell lysates.

The above-mentioned probes and their "negative controls," were used in a solution hybridization (adapted from Kohne and Kacien, supra), to detect spore-forming SRBs (*Desulfotomaculum*), or *Desulfovibrio desulfuricans*.

A "Type II" negative control probe is constructed so that it is complementary to the target but with the same polarity. This is the same as using an experimental probe with reversed polarity.

In summary, a "Type I" negative control probe is constructed so that it is identical in sequence to the intended nucleotide target, but of opposite polarity. This probe has similar characteristics to the experimental probe, but it will not bind to the target, and hence yields a negative result.

Negative control probes of this invention are illustrated as follows: An oligonucleotide probe (5' CCCTCTCAGGCCGGCTACCCATCGTCGCCTT 3')

and it's Type I negative control probe (5' GGGAGAGTCCGGCCGATGGGTAGCAGCGGAA)

were labelled with $^{32}$P and used to detect bacteria in solution hybridization assay in distilled water using hydroxyapatite. See the following text imported from our U.S. Pat. No. 5,049,489 for a description of the assay. Signal was 19,601 cpm for the experimental probe compared to 1692 cpm for the negative control. Since the experimental and control probes are analogous in almost every respect, and negative control probe does not bind to genomic DNA, we can conclude that approximately 1692 cpm of the 19,601 cpm signal from the experimental probe was due to background. Background can be due to a number of causes including insufficient washing to remove unbound probe, non-specific binding of the probe, or trapping of the probe by bacterial debris or other components in the sample.

In environmental samples, experimental signal and/or background can be increased or decreased compared to results using the same bacteria in distilled water. This can be assessed by running a negative control along with the experimental treatment. This was illustrated by resuspending bacteria in oilfield produced water instead of distilled water. Using produced water the signal was 9230 cpm using the experimental probe and 1435 cpm using the negative control probe. Signal from the experimental probe was reduced in oilfield produced water, but background was not changed substantially. Other oilfield produced waters yield different responses that must be assessed on a case by case basis.

Probably the most common means of providing a negative control in hybridization is to use an unrelated probe as the negative control. For example, if the purpose of the assay is to detect sulfate-reducing bacteria in oil production systems, it would be possible to use a probe against a human pathogenic bacterium, or some other bacterium that one would not expect to find in oil production systems. There is often a problem with this, however. Each probe will function correctly under a very specific set of conditions of temperature, composition of the hybridization buffer, and so on. Running experimental and control hybridizations under different conditions is usually so inconvenient that it is impractical. Even if the experimental and control probes are optimized for the same conditions, if the probes are dissimilar in length, distribution of GC and AT, or any of the other variables that affect hybridization kinetics, the probes will behave differently in hybridization, diminishing the value of the negative control.

This problem can be resolved by use of Type I and II negative control probes described herein. These probes are analogous in almost every respect to the experimental probes, except in their inability to bind the intended nucleic acid target. In addition, if there is non-specific probe binding, probe trapping, or insufficient washing, the experimental and negative control probes will respond in the same way. Use of a negative control probe allows one to accurately determine how much of the experimental signal is due to binding of the experimental probe to the target nucleic acid. Without negative controls it is difficult to determine how much of the signal from a hybridization assay is due to background. This can be crucial because in some environmental samples high signal is due entirely or almost entirely to high background. Thus, negative controls can be crucial to interpretation of results from hybridization assays.

The criteria described herein for design of negative control probes are superior to the prior art.

A negative control probe was used in a hybridization assay by Giovannoni et al. in J. Bacteriol. 170:720–726 (1988). This control probe was described as "complementary to the universal probe (i.e., it was rRNA-like, as opposed to complementary to the rRNA) . . . it should be incapable of hybridizing with the rRNA." The accompanying figure indicated that their "background control" sequence was complementary in part to their probe. However, negative control probes complementary in sequence and polarity to the target will bind to the genomic DNA "sense" strand, providing some conflicting signal in the hybridization assay, which is undesirable. The Types I and II negative control probes described herein are superior to the background control probes of Giovannoni et al. since there is no signal contribution from genomic DNA.

Synthetic targets

Type I and II negative control probes have an inherent potential use as synthetic "targets." Normally, low signal from the negative control probe and high signal from the experimental probe indicates that the assay is working correctly, and that the signal from the experimental probe is due to hybridization rather than non-specific binding of probe to impurities in the sample, or to other confounding factors. A defective, negative control probe, or a defective label or reporter group on the control probe, however, could yield the same result, leading one to believe that signal from the experimental probe indicated a "true positive" when in fact the signal was a "false positive."

A convenient way to test negative control probes would be by the use of synthetic targets complementary to the negative control probes. These target sequences could be added to a replicate of the sample to be tested. If the negative control probe yielded a "positive" result in sample replicates where the synthetic "target" was added, and a "negative" result in replicates where the synthetic "target" was not added, this would indicate that the negative control probe was functioning properly. Use of synthetic targets would be especially convenient for use in homogeneous assays in which bound and unbound probe need not be physically separated. The short length of an oligonucleotide hybrid between the experimental probe and its complementary target can preclude separation using hydroxyapatite which binds relatively long, double stranded nucleic acids. We believe, however, that the main use of oligonucleotide probes will be in homogeneous hybridization assays, and Type I and II target sequences should be ideal for testing negative control probes in these assays. Synthetic targets can be incorporated into longer sequences where this is advantageous. For example, the synthetic target sequence can be appended to or included within a longer sequence with regions that are complementary, forming double stranded regions that would bind to hydroxyapatite, enabling separation of bound and unbound probe.

Synthetic target sequences could be used to test negative controls in a variety of hybridization methods in addition to assays designed to detect ribosomal RNA. Illustrative examples of a "Type II" negative control probe sequences are:

| | |
|---|---|
| 3' ACGGGCGGTGTGTRC 5' | Type II negative control probe for Universal C probe |
| 5' TGCCCGCCACACAYG 3' | Synthetic complement (target) for the above negative control probe (note that this is the Type I negative control probe). |

The Type I negative control probe could be used as a target for the Type II negative control probe, and conversely, the Type II negative control probe could be used as a target for the Type I negative control probe.

One advantage of the above design of the negative control probe and the synthetic target of that probe is due to the fact that all three probes (test probe, negative control probe, and the complement of the negative control) could be used under the same hybridization conditions because they have similar characteristics—the same length, the same GC/AT ratios, and also the same distributions of G or C and A or T along the length of the probe. Therefore the three different probes behave similarly under the same hybridization conditions. This has practical utility because one set of hybridization conditions can be used for the test assay and the control assays, which simplifies the procedure.

It is anticipated that there are instances where it would be desirable to use synthetic target sequences that are shorter or longer than the negative control probe length. Longer synthetic target sequences could be used to simulate secondary and tertiary structure of the target nucleic acid being assayed, where secondary and tertiary structure enhances or diminishes probe access and/or binding.

Synthetic target sequences shorter than the negative control probe could also be used, for example, where it is desirable to diminish signal from the negative control probe. This could be useful, for example, in assays where rRNA secondary and tertiary structure competes with the experimental probe, reducing its signal. It might be desirable in this case to also reduce signal from the hybrid between the negative control probe and the synthetic target sequence.

Synthetic oligonucleotide targets or negative control probes could include a "tail" that could be used for hybridization with another probe used for signal amplification or other purpose. The "tail(s)" could comprise a region that would "snap back" into a double stranded structure if regions of duplex are desirable. Large regions of duplex might be used, for example, to enable removal of synthetic targets using hydroxyapatite.

Nucleic acid structural analogues.

Type I and II negative control probes are useful for hybridization assays, but potential uses of these design criteria go beyond the specific applications in hybridization assays. Probe design referenced to a specific structure is illustrated in the drawings and explained in more detail below.

DETAILED DESCRIPTION OF THE DRAWINGS

Figure 1:
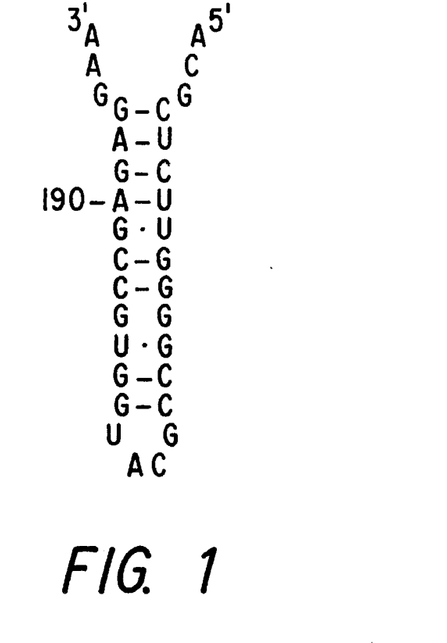
FIG. 1 illustrates the secondary structure of a naturally occurring rRNA, a small part of 16S rRNA of a sulfate-reducing bacterium.

Type I and II probe designs produce analogues to nucleic acid secondary and tertiary structures, as well as to primary structure. Secondary structure for a small part of 16S rRNA of a sulfate-reducing bacterium (Desulfotomaculum), is illustrated in FIG. 1.

Figure 2:
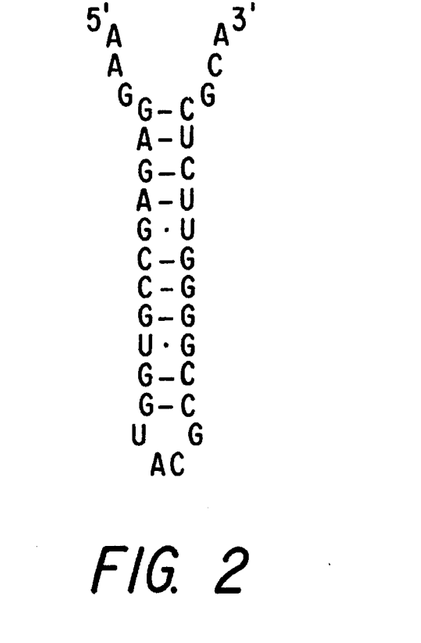
FIG. 2 a Type I negative control probe, shows a reverse sequence to the naturally occurring rRNA of that of FIG. 1.

Primary, secondary and tertiary structure analogous to this naturally occurring rRNA can be produced by Type I design criteria, i.e., by reversing sequence polarity of the "target" molecule (FIG. 2). This results in a sequence that does not occur naturally, and will not bind to genomic nucleic acid or the rRNA.

Figure 3:
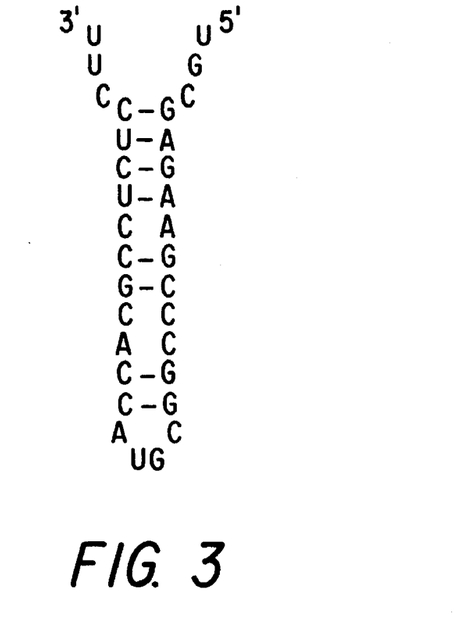
FIG. 3 shows a Type II negative control probe, a complementary sequence but with the same polarity as the original structure of FIG. 1.

Analogous structure can also be produced by Type II design criteria, i.e., by producing a complementary sequence but with the same polarity as the original structure (FIG. 3). This too results in a sequence that does not occur naturally and will not bind to genomic nucleic acid or the rRNA.

Figure 4:
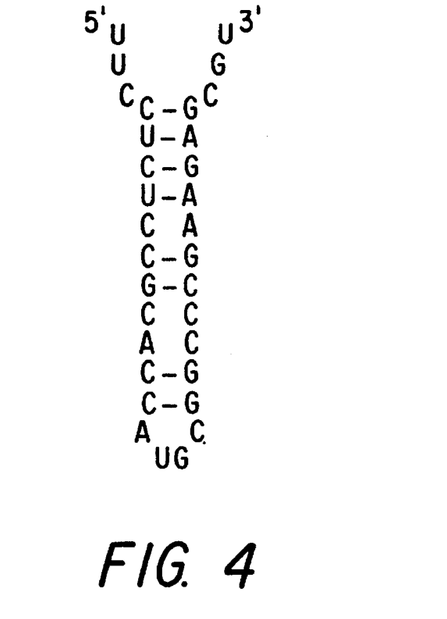
FIG. 4 shows an analogous structure of synthesized nucleic acid with a sequence complementary to the naturally occurring rRNA of FIG. 1.

Finally, an analogous structure could be produced by synthesizing a nucleic acid with a sequence complementary to the naturally occurring rRNA (FIG. 4). This is unlike the two previous constructs since it results in a naturally occurring sequence that would bind to genomic nucleic acid and the rRNA.

FIGS. 2–4 are depicted as RNA, although their depiction as DNA might be more relevant since synthetic DNA is typically used in hybridization assays.

Sequence and structural analogues produced by Type I and Type II design criteria have potentially wide ranging applications in addition to their utility in nucleic acid hybridization assays. Key biological processes are regulated by RNA or ribonucleoprotein. Specifically, it has been reported that the "RNA polymerase III transcription machinery includes an essential nucleic acid component," (Hoffman, M. 1991. An RNA first: It's part of the gene-copying machinery. Science 252:506–507).

Analogous structures of the kind described herein could be useful for studying the assembly and/or interaction of these ribonucleoprotein particles or complexes. For example, if the RNA described in Young et al. (1991. A class III transcription factor composed of RNA. Science 252:542–546), "functions primarily as a structural scaffold on which polymerase III and other protein components of the transcriptional machinery are hung," the design criteria described herein could provide alternative, synthetic, analogous structures. Similarities and differences between the naturally occurring molecule(s) and the analogues described herein could be exploited. For example, analogues of the kinds described herein would be similar in structure to the original molecule(s). The extent to which structure contributes to the function could be studied by using structures synthesized using Type I and II design criteria. Thus a structural analogue to the original molecule could be invaluable for study to determine whether the functioning of the molecule is due to structural scaffolding provided by DNA/RNA. Functioning of these molecules could be studied, and altered, by selective modification of the structural analogues described herein. The constructs maintain alternative secondary and tertiary structures, which may be required for functioning of the molecule. Analogous structures may confer controllable differences in ribozyme cleavage, protein binding, and susceptibility to enzyme activity.

These structural analogues may allow control of transcription in vivo or in vitro by selective enabling or disabling of processes dependent upon nucleic acid structure (primary, secondary and/or tertiary).

Specific embodiments of the invention include:
1. DNA sequences
2. Mixed DNA/RNA sequences
3. Sequences containing nucleoside analogues
4. Sequences containing substitutions
5. Maintaining G/U pairs rather than complementing them
6. Substituting G for U and U for G in U/G pairs.
7. Nucleoside substitutions introduced into analogous sequences/structures designed using Type I and II design criteria, to deliberately and selectively modify part of a structure.
8. Inclusion or appending of sequences into sequence/structural analogues to facilitate, maintain, or restore capability for binding to other nucleic acid sequences
9. Inclusion of a sequence produced by Type I or II design criteria as part of a larger structure, sequence, or association.
10. Producing a sequence (structure) analogous to all or only part(s) of a naturally occurring sequence (structure).

To facilitate a complete understanding of the invention, there follows a description of relevant portions of our U.S. Pat. No. 5,049,489 the entire disclosure of which is hereby incorporated by reference.

Application of oligonucleotide probes complementary to regions of the 16S rRNA molecule for the identification of specific organisms or groups of organisms has been described by Gobel et al. in *J. Gen. Microbiol* 133:1969–1974 (1987), Haun and Gobel in *FEMS Microbiol. Letters* 43:187–193 (1987), Giovannoni et al. in *J. Bacteriol.* 170:720–726 (1988) and Stahl et al. in *Appl. and Environ. Microbiol.* 54:1079–1084 (1988). These authors recognized the value in targeting the 16S rRNA molecule because it contains ribonucleotide sequences unique to particular taxa, and because this molecule is present at about 10,000–20,000 copies per cell as described in Stahl, (1986) *Bio/technology* 4:623–628. There are only about 7 copies of the 16S rRNA gene in the genome (Ingraham et al., 1983, Growth of the Bacterial Cell), and thus the rRNA targets are greatly amplified by comparison.

The assay procedure enables a quick means to identify a class of bacteria of specific interest and arises from procedures used to classify organisms taxonomically. Elucidation of phylogenetic relationships among organisms has been greatly aided by analysis of rRNA because the sequences encoding rRNAs change very slowly compared to most proteins (reviewed in Fox et al., *Sci.* 209:459–483 (1980)). In particular, the approximately 1600 nucleotide-long 16S rRNA gene has been used extensively to ascertain bacterial phylogenies in a procedure known as 16S rRNA oligonucleotide catalog analysis. In practice, $^{32}$P-labelled 16S rRNA is digested with ribonuclease T1 (which cleaves the molecule at G residues) and the resulting short fragments of up to 20 nucleotides are separated by two dimensional paper electrophoresis and are subsequently sequenced. A catalog of these sequences unique to the organism is produced. Direct sequencing of the 16S rRNA molecule using methods like those described in Lane et al., *Proc. Natl. Acad. Sci. USA* 82:6955–6959 (1985), has largely replaced oligonucleotide catalog analysis.

Comparison of the 16S rRNA sequences, some of which are highly conserved among all organisms, and some are divergent, can be used to assess the phylogenetic relatedness between the organisms. Using this technique, some 400 bacterial species have been analyzed, including the delta group of the purple bacteria, a newly recognized group composed of the sulfur- and sulfate-reducing bacteria myxobacteria, and bdellovibrios, as described by Oyaizu and Woese, *System. Appl. Microbiol.* 6:257–263 (1985). The sulfate-reducing bacteria in this group of purple bacteria are non-spore forming, gram-negative and grow at mesophilic temperatures. Fowler et al., *System. Appl. Microbiol* 8:32–41 (1986) recognized seven genera that included Desulfovibrio, Desulfococcus, Desulfosarcina, Desulfomonas, Desulfobulbus, Desulfonema and Desulfobacter. Another group of SRBs has been defined as belonging to the genus Desulfotomaculum. This genus is spore-forming, gram-positive and it grows at mesophilic or thermophilic temperatures. Both the spore-forming and non-spore-forming groups of SRBs have been implicated in causing corrosion and producing hydrogen sulfide and ferrous sulfide in oilfield oil and water handling facilities.

The procedure uses novel probes for the sulfate-reducing bacteria described herein prepared on the basis of and corresponding to unique, recognizable base sequences in a portion of the 16S rRNA of an SRB of interest. Each probe has complementary base sequences that will hybridize to 16S rRNA base sequences from the bacteria of interest. The probe preferably has at least one identifiable, detectable label attached to it. Oligonucleotides that are of opposite polarity to either the target rRNA or the probe are described above. Their function is to serve as negative control probes in parallel assays with the target-specific probe, to discriminate true positives from background signal. Use of negative control probes and techniques to prevent gram positive bacteria from interfering with analyses are particularly useful with crude environmental samples.

The procedure for determining the presence of sulfate-reducing bacteria in a test sample includes making a lysate of the bacteria contained in a test sample and binding the RNA in the lysate to a solid support. The attached test sample extract is exposed to an oligonucleotide DNA probe composed of a nucleotide sequence substantially complementary to the specific nucleotide sequence of a portion of the 16S rRNA molecule of the sulfate-reducing bacteria to be assayed. The nucleotide sequence of the probe is capable of hybridizing or base pairing with the complementary sequences of the 16S rRNA molecule to be assayed. The probe also includes a detectable label. The solid carrier plus attachments is rinsed to remove any probe not hybridized to the test sample, removing any unattached labelled probe that would otherwise interfere with correct readings. The carrier is then assayed for the presence of the probe which indicates qualitatively and quantitatively the presence of the SRB of interest. Procedures for determining total bacterial counts based on probes for portions of the 16S rRNA molecule common to all bacteria are also described.

The probe binds to ribonucleotide sequences in the 16S rRNA molecule. The procedure utilizes specific DNA oligonucleotide probes complementary to the 16S rRNA molecule to specifically identify the sporing sulfate-reducing bacteria and a member of the non-sporing sulfate-reducing bacterium, *D. desulfuricans*, for rapid and accurate identification, both qualitative and quantitative, in a sample suspected of containing SRBs using filter, solution, or other hybridization methods employing a radioactive or non-radioactive detection system. Our filter-based detection system is based upon one used to detect messenger RNA in an RNA colony hybridization method developed by Ivanov and Gigova, *Gene* 46:287–290 (1986), adapted by us to be used with rRNA. For solution hybridizations, we used a format adapted from published European patent application 0,229,442 (Kohne and Kacien, 1987).

The probes used are based on the 16S rRNA sequences capable of specifically identifying the sporing and one of the non-sporing sulfate-reducing bacteria for rapid and accurate identification, both qualitative and quantitative, in a sample suspected of containing SRBs using a filter or solution hybridization method employing radioactive or non-radioactive detection systems.

The probes were selected or prepared, as the case may be, after sequence analysis of the 16S rRNA molecule. In some instances it was necessary to first isolate a candidate bacterium and sequence its 16S rRNA molecule as described in Lane et al., *Proc. Natl. Acad. Sci. U.S.A.* 82:6955–6959 (1985). Use was also made of sequence data available from the literature.

Once synthesized, the candidate probes were tested against partially purified RNA obtained from known SRBs using a dot blot assay with $^{32}$P-labelled DNA probes. The primary reagent is the labelled oligonucleotide DNA probe of approximately of 15–31 nucleotides. The probe is substantially complementary to the 16S rRNA molecule. The probe is obtained from 16S rRNA according to published procedures and is synthesized to be complementary to a predetermined sequence to accurately target and hybridize to rRNA from the particular SRBs and groups of SRBs that are to be detected and/or quantitated. The probe is labelled with a convenient marker that is itself non-reactive, readily available, easy to use, and reliable. Ligands such as biotin, thyroxine and cortisol or other linkers may be used to attach the marker to the probe. Enzymes of interest as labels are primarily hydrolases, particularly the esterases and glycosidases, or oxidoreductases, particularly peroxidases. Fluorescent compounds useful as labels include fluorescein and its derivatives, and rhodamine and its derivatives, among others. Chemiluminescent compounds and antibodies could also be utilized in a labelling/detection system. Alternatively, the probe is labelled with a radioactive isotope such as $^{32}P$, $^{3}H$, $^{14}C$, $^{125}I$, $^{35}S$ or other such nuclide. Any radioactive label may be employed which provides for an adequate signal and has sufficient half-life.

Briefly, the procedures for identifying sulfate-reducing bacteria, or other bacteria of interest, using oligonucleotide DNA probes complementary to the 16S rRNA molecule are as follows: a sample thought to contain the SRB of interest is treated with the lytic agent to expose the 16S rRNA molecule. In one embodiment, total cellular RNA is fixed to a suitable support, e.g., a nitrocellulose or nylon membrane. Oligonucleotide DNA probes with base sequences complementary to a portion of the 16S rRNA molecule are hybridized to the rRNA, which is attached to the support. Unhybridized probe is then washed away since it is not bound to the solid support-rRNA complex. Alternatively, any method that would destroy or interfere with signal from unhybridized probe could also be used to enable detection of signal specifically from bound probe. The use of nucleic acid probes to detect SRBs is not limited to the use of any particular labelling or labelling/assay system. The label is "read" and quantified using usual procedures.

The particular hybridization technique used is not essential to the invention. Generally, substantial excess over stoichiometric amount of the probe will be employed to enhance the rate of binding to the fixed RNA in hybridization assays.

Preparation of cells impinged on nitrocellulose filter paper: Cells from pure culture isolates of SRBs (positive controls) as well as from nonrelated bacteria, for example, E. coli and B. subtilis (negative controls), or from environmental samples, are filtered onto a nitrocellulose membrane (0.22 or 0.45 μm pore diameter). The membrane is placed on Whatman 3 MM filter paper soaked in 10% sodium dodecyl sulfate (SDS) for 5 minutes at room temperature, after which it is transferred to a filter paper (Whatman 3 MM) soaked in 3×SSC (1×, 0.015M sodium citrate, 0.15M sodium chloride, pH 7.6) at 65° C. for 15 minutes. A hooded slide warmer maintained at 65° C. is used for stable temperature maintenance. The nitrocellulose filter paper with the impinged cells on it is dried at 37° C. for 10 minutes, vacuum dried 15 minutes at 70° C., and stored under vacuum until use. Cells may be impinged on nitrocellulose filter paper contained in a dot blot apparatus, or on circular filters of 2.4 cm for larger volume application.

Hybridization of labelled probe target: The target (16S rRNA) from the sample to be assayed is bound to the nitrocellulose filter paper during the above treatment. The filters are prehybridized in a solution composed of 1M NaCl, 0.1% SDS and 50 μg/ml of polyA RNA for 1 hour at 65° C. Hybridization with probe end-labelled with [gamma-$^{32}P$] ATP is carried out for two hours at a temperature dependent on the nucleotide base composition of the probe as determined from the formula reviewed in Meinkoth and Wahl, Anal. Biochem. 138:267–284 (1984):

$$T_h = 4(G+C) + 2(A+T) - 5° C.$$

where G, C, A and T are the number of corresponding nucleotides in the probe.

The filters are then washed twice for 15 minutes each at a temperature of $T_h + 5°$ C. These temperatures are initial approximations that may be adjusted based upon results. Filters are then air dried briefly, placed onto a cellulose acetate backing or other suitable backing, covered with Saran wrap and exposed to X-ray film at –80° C. using an intensifying screen.

The probes specific to the SRBs described herein and used with our modification of the RNA colony hybridization protocol of Ivanov and Gigova (supra) permit a lower limit of detection of about $1 \times 10^6$ cells impinged on the filter when the probe is labelled with $^{32}P$.

The probes used are specific to the 16S rRNA region of interest in the SRB or target bacteria and may be prepared as described below.

A region of the 16S rRNA molecule that is specific for the bacterial isolates that we are treating as D. desulfuricans was determined as follows: Desulfovibrio desulfuricans sequences for a region of 16S rRNA which is highly variable as described in Woese et al., Microbiol. Rev. 47:621–669 (1983) and Stahl et al., Appl. and Environ. Microbiol., 54:1079–1084 (1988) (about bases 180–220 based on E. coli secondary structure) were obtained from the literature (Oyaizu and Woese, supra) for American Type Culture Collection (ATCC) 27774, and from our own sequencing for ATCC 13541 and an oilfield isolate identified as 22681B. The sequences were obtained using the method of Lane et al. (supra), in which total cellular RNA is isolated and the 16S rRNA molecule is the template for a DNA sequence complementary to the rRNA. The DNA is then sequenced using the dideoxy chain termination method, which was adapted from Sanger et al., Proc. Natl. Acad. Sci. U.S.A. 74:5463 (1977). Both oilfield isolate 22681B and ATCC 13541 that we sequenced show two and possibly three base differences compared to ATCC 27774 in this region of the rRNA, which makes their sequences slightly different from that previously reported for ATCC 27774. The specific sequences are shown below. (Note: numbering is based on 16S rRNA of E. coli, as is standard in the field, and consequently the numbers of nucleotides between two numbered positions may vary depending upon the topology of the particular rRNA).

```
        184                                              219
         |    (G)                                         |
5'  CUCAAGAUNAACUUUUUGAGGAAAGAUGGCCUCUGCUUGCAU-CUAUC  3'      22681B
    :::: :: ::  :::::::::::::::::::::::::::::: :::::
5'  CUCAAAAUGAACUUUUUGAGGAAAGAUGGCCUCUGCUUGCAUGCUAUC  3'      ATCC 27774
    :::: :: ::::::::::::::::::::::::::::::::::: :::::
5'  CUCAAGAUNAACUUUUUGAGGAAAGAUGGCCUCUGCUUGCAU-CUAUC  3'      ATCC 13541
              (U)
```

The colons between the sequences indicate sequence identity; N represents any one of the four bases, and is probably G in 22681 B and U in ATCC 13541. The (–) in 22681 B and ATCC 13541 at the position of ca. 214 means that the base is missing compared to the G at the same position in ATCC 27774.

Although there are a few base changes among these three isolates in this 49-base-long region, other non-spore-forming SRBs (from the data base of R. Devereux, Environmental Protection Agency, unpublished) show four or more changes. A probe complementary to bases between the arrows in the above figure, however, shows 100% sequence identity among the three isolates.

In practice, we have shown in filter hybridizations that the following probe, which was complementary to bases 198–214 of ATCC 27774 (*E. coli* 16S rRNA numbering system), correctly detected ATCC 13541, 22681B and other oilfield isolates that we are treating as *Desulfovibrio desulfuricans*. The probe sequence is as follows:

(5' ATGCAAGCAGAGGCCATC 3')

The above probe did not cross react with bacteria from other genera.

DNA probes complementary to predetermined regions of the 16S rRNA molecule may also be used to quantitate sulfate-reducing bacteria. These particular probes will be useful in determining total spore-forming SRB counts in a sample in a relatively short period of time.

We sequenced the 16S rRNA molecule from spore-forming SRBs that were isolated from oilfield water samples and also from ATCC strains. A nearly complete 16S rRNA sequence from ATCC 19858 is shown folded into secondary structure in FIG. 1 of our U.S. Pat. No. 5,049,489. These sequences were compared to 16S rRNA sequences available from the literature and elsewhere to locate specific nucleotide sequences that are shared in common among sporing SRBs, and not found in the 16S rRNA of other bacteria.

We identified a region of 16S rRNA sequence that can be used for detecting, quantitating, and/or distinguishing spore-forming SRBs. The sequence was shared in common among six spore-forming SRB isolates including two ATCC *D. nigrificans*, *D. ruminis* (*D. ruminis* sequence obtained from R. Devereux, unpublished), and three thermophilic spore-forming SRBs isolated from oilfield waters. This sequence comprises nucleotide positions 273–303 (*E. coli* numbering system). The sequence from which a probe was designed is:

```
    273                              303
     |                                |
5' AAGGCGACGAUGGGUAGCCGGCCUGAGAGGG 3'
``` and the probe itself is:

```
    303                              273
     |                                |
5' CCCTCTCAGGCCGGCTACCCATCGTCGCCTT 3'
(SEQ ID NO:1)
```

This probe, referred to here as the "spore-forming SRB probe" showed specificity against laboratory cultures of Desulfotomaculum that were retained on a filter and lysed in situ using guanidinium isothiocyanate in the protocol of Gobel et al., *J. General Micro.* 133:1969–1974 (1987). Lysis of the cells in guanidinium isothiocyanate followed by application of the cells to the filter gave the same result: the limit of detection was equivalent to $5 \times 10^5$ cells impinged on the filter.

The spore-forming SRB probe has been tested against isolated RNA from selected spore-forming SRB isolates as well as from two ATCC isolates. In addition, the probe was tested against isolated RNA from negative controls which included: *E. coli*; an isolate of *Desulfovibrio desulfuricans* from ATCC; and other oilfield isolates identified as Desulfovibrio. This probe successfully identified the spore-forming SRBs (Desulfotomaculum), with minimal cross-reactivity to negative controls. Further, the sequence of the 16S rRNA molecule complementary to the spore-forming SRB probe was compared to available sequences for the same region from thirty-three 16S rRNA sequences of bacteria representing diverse eubacterial and archebacterial genera. This sequence was found to be distinctive of the spore-forming SRBs, with the exception of *Desulfotomaculum orientis*, which shows a two-base difference in this region (according to R. Devereux, unpublished). We noted that gram-negative bacteria showed greater than 3 base differences in this region of the molecule, but that some gram-positive bacteria showed only three or fewer base differences in this region. A more extensive sequence database might possibly reveal gram-positive bacteria with 100% sequence identity to the spore-forming SRBs in this region. This would not negate the general utility of this probe unless these other bacteria were present in high concentrations in the systems to be tested for SRBs. We have, however, devised a means of excluding these other bacteria from an assay should they be present in a sample also suspected of containing SRBs.

The means by which gram-positive bacteria other than Desulfotomaculum are excluded from the gene probe assay resides in the cell lysis step preparatory to gene probe analysis. Desulfotomaculum is unusual among gram positive bacteria in having gram positive cell wall ultrastructure but yielding a negative gram stain and lysing easily. Neither quanidinium isothiocyanate nor a lysis buffer containing 20% SDS (sodium dodecyl sulfate) lysed representative gram-positive bacteria, however, both lytic agents solubilized Desulfotomaculum and the gram negative SRB, Thus, use of lytic agents that lyse Desulfotomaculum without lysing most other gram positive bacteria will eliminate a possible source of false-positive signal generation in assays for sporing SRB As an illustration of this, representative gram-positive bacteria and SRBs were exposed to the lytic agents quanidinium isothiocyanate or 20% SDS. The gram positive bacteria tested were Peptococcus isolate MO6182, Propionibacterium isolate M19782, Micrococcus isolate 21482, *Bacillus subtillis* (ATCC 6051, *Bacillus stereothermophilus* (1503 NCA), Bacillus isolate 16982, Clostridium isolate T06582, and *Clostridium thermophilius*, ATCC 7957. The thermophiles *B. stereothermophilus* and *C. thermophilius* lysed in both lytic agents whereas the other gram positive isolates, including the thermophilic Clostridium T06582, did not.

If cells from field samples are lysed in the appropriate reagent, in this case in either guanidinium isothiocyanate or 20% SDS as summarized above, most kinds of gram positive bacteria probably will be recalcitrant to lysis. Thus, their 16S rRNA will not be available to hybridize with the spore-forming SRB-specific probe, and false-positive signal generation resulting from possible cross-reactivity of the probe is eliminated automatically.

We also constructed a probe that differentiates two sulfate-reducing spore-forming SRB thermophile isolates. A region of 16S rRNA that shows probable 100% sequence identity between two oilfield thermophilic SRB isolates previously identified as members of the genus Desulfotomaculum based on morphological and biochemical characteristics is located at bases 139–183 (*E. coli* numbering system). ATCC cultures of Desulfotomaculum species including *D. nigrificans, D. orientis* and *D. ruminis* show at least 5 base differences in this region. However, these two isolates differ from one another in other regions of the molecule including the region from position 180 to 220. Therefore, according to phylogenetic relationships based on 16S rRNA (Oyaizu, supra), these spore-forming SRB thermophiles show a close relatedness to each other but are enough different from ATCC type species of Desulfotomaculum and each other that they may represent new species or even a new genus. The 16S rRNA target sequences from the two thermophiles are:

Isolates:

T 35282:
```
     139                                                           182
      |                                                             |
5' UAAGACCGGGAUAACACCUCGAAAGGGGUNCUAAUACUGGAUAAG 3'
   : : : : : : : : : : : : : : : : : : : : : : : : : : : : : : : : : : : : : : : : : : : :
T1:
5' UAAGACCGGGAUAACACCUCGAAAGGGGUNCUAAUACUGGAUAAG 3'
                 |           |
                 U          G/U    U
```

In this representation N designates any of the 4 bases. In T1, at positions marked with a bar (|), the base is most probably A or U, and the second bar, N is most probably either base G or U. A probe made from this sequence has been tested with isolates 35282 and T1 and other spore-forming SRB thermophiles and ATCC *D. nigrificans* in the RNA cell immobilization blot hybridization described above. The probe sequence is:

```
    164                    141
     |                      |
5' CCTT/ATCGAGGTGTTATCCCGGTCT 3'
``` where the underlined T/A means that during synthesis, either an A or a T should be inserted such that 50% of the molecules have a T at this position and 50% have an A. This probe correctly identified isolate T1 and 35282 and did not react with any of the other isolates. Thus, this probe will be useful in identifying spore-forming SRBs with this particular complementary sequence on the target 16S rRNA. As such, it will be useful in tracking some members of the thermophilic spore-forming population that are present at Prudhoe Bay and perhaps in other environments.

Both the spore-forming and *D. desulfuricans*—specific sulfate reducing bacterial probes described above will be used to assay cell numbers in the raw environmental samples. It will also be informative to know the total bacterial count in these samples. For this reason, another probe suited to the procedures of this invention is called Universal C. Lane et al. (supra) proposed this sequence as a "universal" primer for rRNA sequencing reactions, but did not point out that this sequence could also be used as a probe to detect phylogenetically diverse taxa. This probe identifies bacteria, archebacteria and eukaryotes—in fact all living cells—and may be used to enumerate and quantitate total bacteria and all living cells, including fungal and yeast cells in a sample. The "Universal C" probe is:

5' ACGGGCGGTGTGTRC 3' where R is A or G.

The 16S rRNA molecule has constant and variable regions from which probes may be designed depending on the region(s) of interest. Variable regions are used to identify specific organisms in a gene probe assay, the more constant regions to identify members or groups of related organisms at higher taxanomic levels. Three relatively constant regions, termed Universal A, B and C (Lane et al., supra), have been identified and used as primers in sequence analysis of the 16S rRNA gene itself and all three primers are useful in sequencing the 16S rRNA molecule. Of these constant regions, the Universal C probe as above is the most sensitive regarding detecting its target on the 16S rRNA molecule. Its sequence position on the *E. coli* 16S rRNA, the standard for all comparisons, is 1392–1406.

We now describe using the Universal C probe as an alternative to doing total bacterial counts, such as routinely conducted in the nutrition and oil industries or anywhere a total bacterial count is needed. Because of its short time of assay, as short as 2–3 hours, as compared to 1–5 days for conventional procedures, this probe will be extremely useful.

Universal primers A, B and C were compared relative to their limits of detection using 10-fold serial dilutions of bacterial cultures (*E. coli*) in our modified RNA colony hybridization assays and detection limits were about $1 \times 10^5$ cells impinged with Universal C, which was shown to be superior to A and B. A limit of detection of $1 \times 10^4$ cells impinged on a filter was achieved with Universal C when *Pseudomonas deovorans* was tested. Universal C always identified its target in colony hybridizations of sporing and non-sporing bacteria, and was especially noted under conditions where other less sensitive probes did not identify their targets as well.

The following is an example of the way that nucleotide probes could be used to detect SRBs; however, other techniques for performing the assay such as particular hybridization conditions or techniques, solid supports used for immobilizing nucleic acids, or means of separating probe-rRNA complex from unbound probe are contemplated.

SRBs were grown in liquid culture as described in Postgate, J. R., "The Sulphate-Reducing Bacteria", Cambridge University Press, Cambridge, 1981; medium C. Approximately $10^{10}$–$10^{13}$ bacteria were pelleted by centrifugation and resuspended in a minimum volume of produced water from the Prudhoe Bay oil-water handling facilities. This water had a slight oil film on the surface and contained iron oxide precipitates. The number of bacteria/ml was determined, and the sample was split into experimental and control replicates containing equal numbers of bacteria. These replicates were spun at about 7,000 g (RCF) for about 20 minutes to pellet the bacteria. This produced water "wash" was intended to simulate conditions of testing using samples drawn directly from oil-water handling facilities. Typically, each bacterial pellet was vortexed into 2–3 ml of lysing solution (20% SDS, 0.01M EDTA, 0.07M $NaH_2PO_4$, and 0.07M $Na_2HPO_4$, pH 7). The lysate was incubated at 60° C. for 10 minutes. Lysed bacterial suspensions were stable for at least a week at 4° C. with minimal decrease in assay sensitivity. The lysate was centrifuged at about 3,000 g (RCF) for about 5 minutes, and two 1 ml aliquots of supernatant were removed for hybridization. Labelled probe ($32^P$ end labelled) complementary to 16S rRNA was added to one aliquot and the labelled complement of the probe was added to the other aliquot. The latter probe will not hybridize to 16S rRNA and this serves as a negative control. Hybridization typically is carried out with shaking for 2 hours at room temperature. Aliquots with volumes calculated to correspond to particular numbers of bacterial cells are withdrawn for separation of unbound probe. Typically, lysate corresponding to about $10^{4-10^{10}}$ bacteria is used for each hybridization. Bound probe is separated from the hybridization solution using hydroxyapatite. Hydroxyapatite solutions are prepared by washing hydroxyapatite particles (Bio-Rad Laboratories, Richmond, Calif.; DNA-grade, Bio-Gel HTP), in a "phosphate wash buffer" consisting of 0.07N $NaH_2PO_4$, 0.07M $Na_2HPO_4$, 0.02% SDS, and 0.001% thimerosal, pH 7; decanting the "fines," and adding sufficient wash buffer to equal 0.02 grams hydroxylapatite per milliliter of buffer. One milliliter of this suspension is placed in a 1 ml microcentrifuge tube and spun for 1 minute at about 10,000 rpm in a microcentrifuge to pellet the hydroxylapatite (HAP). The supernatant is discarded and the hybridization mix is transferred to the tube containing the pelleted HAP. This is vortexed at room temperature for 10 minutes, spun at about 10,000 rpm in a microcentrifuge to pellet the HAP, and the supernatant is discarded. One ml of phosphate wash buffer is added to the tube, which is then vortexed for 2 minutes, spun for 1 minute, and the supernatant is discarded. This is repeated once more and the pellet is dispersed in scintillation fluid and counts per minute (cpm) are measured using a scintillation counter. Results are assessed by comparing cpm of the experimental treatment, cpm of the negative control treatment, and the cpm of a "background" treatment which contains only non-radioactive HAP spun out of the HAP-phosphate buffer suspension. If the cpm of the experimental treatment minus background is at least several times the cpm of the negative control minus background, this is regarded as a "positive result," i.e., the probe has hybridized with complementary "target" rRNA, and bacteria have been detected. When signal from experimental and control treatments approaches background, the limit of sensitivity is being approached. A minimum of about $10^5$ bacteria has been "detected" using this approach.

It would be advantageous in many circumstances to be able to detect $10^3$ or fewer bacteria per ml. This can be accomplished by centrifugation, or by filtering of large, known quantities of produced water through filters that will retain the bacteria. In this way, sufficient bacteria can be collected that sensitivity limits of the particular assay may not be a problem in the practical application of this technique.

Although this technique actually measures the number of 16S rRNA molecules from specific groups of bacteria, the signal obtained can be translated roughly into numbers of bacterial cells by comparison with results obtained using known quantities of cultured SRBs.

Solution hybridization results indicate that there is no need to proceed rapidly with the assay procedure after collection of an environmental water sample. *Desulfovibrio desulfuricans* cells were grown in culture, harvested by centrifugation, washed briefly in distilled water, and resuspended in either aerated distilled water or produced water. Assay sensitivity was not diminished by storage of the bacteria for up to 21 hours in aerated water at room temperature. This has practical utility since it would often be difficult to proceed with the assay immediately after taking a sample.

As used herein, the codes for representing the nucleotide sequences are:

| | |
|---|---|
| A = adenine | M = A or C |
| C = cytosine | R = A or G |
| G = guanine | W = A or T/U |
| T = thymine | S = C or G |
| U = uracil | Y = C or T/U |
| | K = G or T/U |
| V = A or C or G, not T/U | |
| H = A or C or T/U, not G | |
| D = A or G or T/U, not C | |
| B = C or G or T/U, not A | |
| N = A or C or G or T | |

Positions of the nucleotides are numbered in accordance with the *E. coli* numbering system.

Types I and II constructs are meant to be used as negative controls in combination with a binding probe to detect the presence of a particular nucleotide sequence. Short sequences have diminished utility as negative controls due to high probability of chance occurrence of complementary nucleotide sequences in samples. For example, a specific sequence of 10 nucleotides would be expected to occur once, by chance, in a random sequence of $4^{10}$ nucleotides. Therefore, in a genome comprising $10^9$ nucleotides, one might expect approximately 1000 chance occurrences of a complementary 10 nucleotide sequence, diminishing the value of the negative control. We prefer probes 15 nucleotides in length or longer. A chance occurrence of a sequence complementary to a 15 nucleotide negative control probe would be expected to occur by chance only once in a sequence of $4^{15}$ nucleotides. Efficacy of probe/negative control combinations is increased by targeting an rRNA sequence, which may be present at $10^4$/bacterial cell, or even greater. This increases signal to noise ratio for shorter probe/control combinations.

Types I and II constructs are intended to be of sufficient length to be of practical use as negative controls in hybridization assays.

What is claimed is:

1. A method of determining the presence or amount of a target nucleic acid nucleotide sequence in a sample by determining the extent of hybridization of a labeled probe to a target nucleic acid, the process comprising the steps of:
   (1) contacting an aliquot of the sample with an oligonucleotide probe that selectively hybridizes to a recognizable base sequence or target, the probe having an identifiable label attached to it;
   (2) determining the amount of signal from labeled probe hybridized to the target;
   (3) contacting an equivalent aliquot of the sample with a labeled nucleic acid negative control probe, wherein the negative control probe has a nucleotide sequence identical to the target sequence of step (1), or substituting U for T, but having 3'–5' or 5'–3' polarity opposite to the polarity of the target nucleotide sequence, or the negative control probe has a nucleotide sequence complementary to the target nucleotide sequence except that the negative control probe has the same polarity 5'–3' or 3'–5' as the target nucleotide sequence;
   (4) determining the amount of signal from the negative control probe; then
   (5) subtracting the amount of signal determined in step (4) from the amount of signal determined in step (2) to determine the amount of hybridization between the probe of step (1) and the target nucleic acid sequence in the sample.

* * * * *